United States Patent
Iijima

(10) Patent No.: US 10,470,737 B2
(45) Date of Patent: Nov. 12, 2019

(54) RADIOGRAPHIC IMAGING APPARATUS, RADIOGRAPHIC IMAGING SYSTEM, AND METHOD FOR CONTROLLING THE SAME

(71) Applicant: CANON KABUSHIKI KAISHA, Tokyo (JP)

(72) Inventor: Tadahiko Iijima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 253 days.

(21) Appl. No.: 15/702,480

(22) Filed: Sep. 12, 2017

(65) Prior Publication Data

US 2018/0070907 A1 Mar. 15, 2018

(30) Foreign Application Priority Data

Sep. 15, 2016 (JP) .................................. 2016-180327

(51) Int. Cl.
*A61B 6/00* (2006.01)
*H04N 5/32* (2006.01)
*H04N 5/232* (2006.01)

(52) U.S. Cl.
CPC ................ *A61B 6/54* (2013.01); *A61B 6/563* (2013.01); *H04N 5/32* (2013.01); *H04N 5/232411* (2018.08)

(58) Field of Classification Search
CPC . A61B 6/54; A61B 6/563; H04N 5/32; H04N 5/232411
See application file for complete search history.

(56) References Cited

U.S. PATENT DOCUMENTS 10,149,659 B1 * 12/2018 Schwartz .................. H04N 5/32
2011/0116486 A1 * 5/2011 Tachikawa ........... A61B 6/4494
370/338

FOREIGN PATENT DOCUMENTS

JP 2006333898 A * 12/2006
JP 2010-240184 A 10/2010
JP 4684747 B2 5/2011

* cited by examiner

*Primary Examiner* — Michael C Bryant
(74) *Attorney, Agent, or Firm* — Canon U.S.A., Inc. IP Division

(57) ABSTRACT

A radiographic imaging system includes a repeater, a radiographic imaging apparatus, and a control apparatus. The control apparatus controls the radiographic imaging apparatus. The repeater controls timing to emit radiation from a radiation source. The radiographic imaging apparatus includes a communication circuit that wirelessly communicates with an external device in a first communication mode and a second communication mode in which power consumption is lower than that in the first communication mode. The radiographic imaging apparatus also includes a communication control unit that controls the communication circuit so that, when receiving an instruction to start preparation for imaging, the communication circuit operates in the first communication mode until receiving a signal for emission of radiation from the repeater.

11 Claims, 13 Drawing Sheets

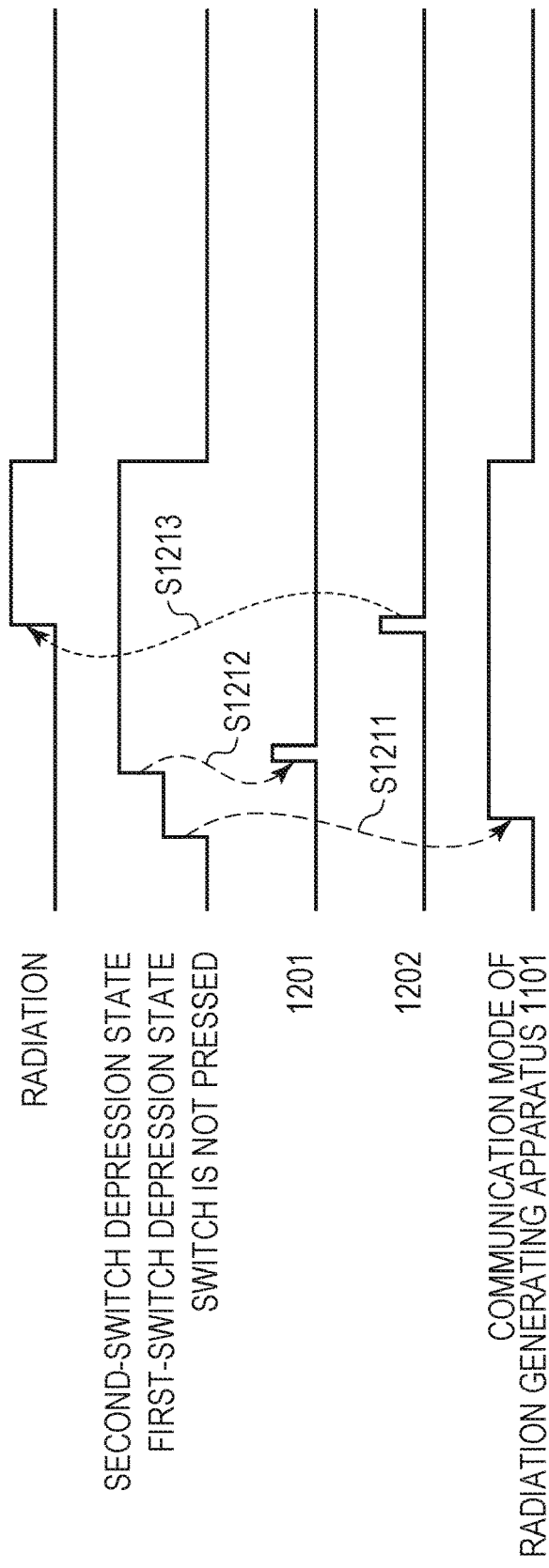

RADIOGRAPHIC IMAGING APPARATUS, RADIOGRAPHIC IMAGING SYSTEM, AND METHOD FOR CONTROLLING THE SAME

BACKGROUND

Field

The present disclosure relates to a radiographic imaging apparatus, a radiographic imaging system, and a method for controlling the same.

Description of the Related Art

There is a known radiographic imaging apparatus that applies radiation to a subject from a radiation generating apparatus and digitizes a radiation image that is an intensity distribution of the radiation that has passed through the subject. A radiographic imaging system that processes the radiation image digitized by the radiographic imaging apparatus and displays it on a display apparatus has been put into production.

Portable radiographic imaging apparatuses with a built-in battery and that wirelessly communicates have recently been developed. To increase the operating time with the battery, such battery-operated radiographic imaging apparatuses can be limited in wireless communication function to reduce power consumption when not in use.

When radiation is emitted at a timing not suitable for imaging, radiographic imaging apparatuses cannot sometimes capture a radiation image or the quality of a captured radiation image is sometimes poor. For these reasons, a known radiographic imaging system controls the radiographic imaging apparatus and the radiation generating apparatus to communicate with each other so that the imaging state of the radiographic imaging apparatus and the radiation exposure timing match.

In a radiographic imaging system disclosed in Japanese Patent No. 4684747, when a radiation switch connected to a radiation generating apparatus is pressed, an imaging request signal is transmitted to a radiographic imaging apparatus rather than immediately emitting radiation from the radiation generating apparatus. After the radiographic imaging apparatus receives the imaging request signal, an imaging preparation completion signal is transmitted to the radiation generating apparatus. The radiation generating apparatus starts to emit radiation in response to reception of the imaging preparation completion signal.

If the wireless communication function of the radiographic imaging apparatus is limited to reduce power consumption, a delay in communication between the radiographic imaging apparatus and the radiation generating apparatus can occur. This can hinder a rapid imaging operation using the radiographic imaging system. In particular, a delay can occur between the time when the user presses the radiation switch and the time when the radiation is actually emitted, which can decrease user convenience and cause unnecessary exposure to the patient due to re-radiographing.

SUMMARY

The present disclosure prevents a delay in radiation emission while reducing power for use in the wireless communication function of a radiographic imaging apparatus.

A radiographic imaging system according to an aspect of the present disclosure includes a repeater, a radiographic imaging apparatus, and a control apparatus. The repeater is configured to control timing to emit radiation from a radiation source. The radiographic imaging apparatus includes a communication circuit configured to perform wireless communication in a first communication mode and a second communication mode in which power consumption is lower than that in the first communication mode. The control apparatus is configured to control the radiographic imaging apparatus. The radiographic imaging apparatus further includes a communication control unit configured to control the communication circuit such that, when receiving an instruction to shift to an imaging possible state, the communication circuit operates in the first communication mode until receiving a signal for permitting emission of radiation from the repeater.

Further features will become apparent from the following description of exemplary embodiments with reference to the attached drawings.

BRIEF DESCRIPTION OF THE DRAWINGS

FIG. 13 is a diagram illustrating the operation of the radiographic imaging system according to the fifth embodiment.

DESCRIPTION OF THE EMBODIMENTS

First Embodiment

Figure 1:
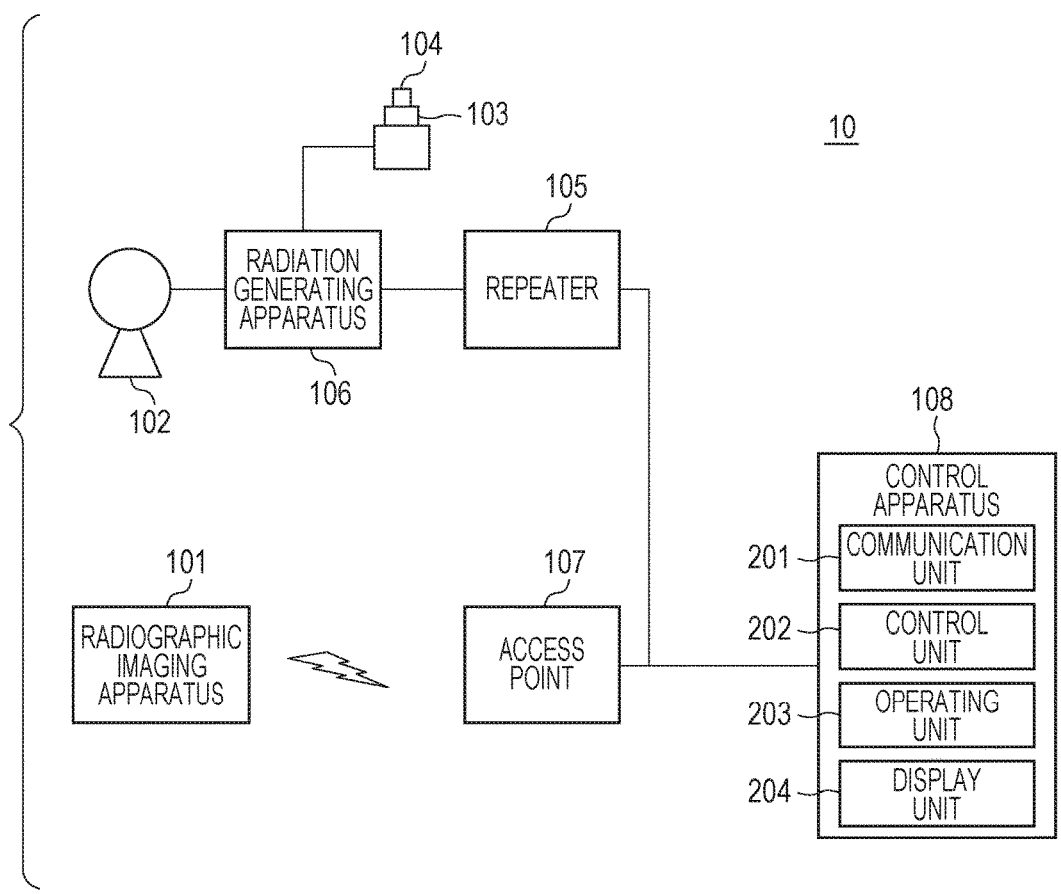
FIG. 1 is a diagram illustrating a radiographic imaging system according to a first embodiment of the present disclosure.

Radiographic imaging systems according to embodiments of the present disclosure will be described hereinbelow with reference to the drawings. FIG. 1 is a diagram illustrating a radiographic imaging system 10 according to a first embodiment.

As illustrated in FIG. 1, the radiographic imaging system 10 includes a radiographic imaging apparatus 101, a radiation generating apparatus 106, a second switch 103 and a first switch 104 connected to the radiation generating apparatus 106, a repeater 105, a control apparatus 108, and an access point 107.

The radiographic imaging apparatus 101 wirelessly communicates with external apparatuses, i.e., the repeater 105 and the control apparatus 108, via the access point 107. The radiographic imaging apparatus 101 receives a state-shift indication signal and a state confirmation signal from the control apparatus 108. The radiographic imaging apparatus 101 transmits acquired radiation images to the control apparatus 108. The state-shift indication signal includes, for example, an indication to shift the radiographic imaging apparatus 101 to an imaging possible state.

The control apparatus 108 wirelessly communicates with the radiographic imaging apparatus 101 via the access point 107. The control apparatus 108 includes a communication unit 201, a control unit 202, an operating unit 203, and a display unit 204. The communication unit 201 is used for communication with the radiographic imaging apparatus 101. The communication unit 201 can be used for connection with the repeater 105 and, for example, a hospital network. The communication unit 201 includes communication hardware, such as a network adapter.

The control unit 202 performs various controls. For example, the control unit 202 controls the state of the radiographic imaging apparatus 101, acquires a radiation image from the radiographic imaging apparatus 101, displays the radiation image, receives an order for imaging from a radiography information system (RIS) terminal, and registers imaging information. The control unit 202 can include a processor, such as a microprocessor, a dedicated circuit, such as an application specific integrated circuit (ASIC), or a combination thereof. The operating unit 203 includes various input devices, such as a keyboard or a touch panel for receiving instructions from the operator. The display unit 204 includes the function of displaying an operating screen and a radiation image and displays the state of the radiographic imaging apparatus 101 and images received from the radiographic imaging apparatus 101.

The radiation generating apparatus 106 controls emission of radiation from a radiation source 102. An example of the radiation source 102 is a radiation tube. The radiation generating apparatus 106 is connected to the first switch 104 and the second switch 103. The first switch 104 and the second switch 103 are formed into a single radiation emission switch.

The first switch 104 is used to instruct the radiation generating apparatus 106 to prepare for emission of radiation when pressed. In response to the instruction, the radiation generating apparatus 106 controls the radiation source 102 to prepare for emission of radiation. The second switch 103 is used to instruct the radiation generating apparatus 106 to emit radiation. In response to the instruction, the radiation generating apparatus 106 transmits a request signal for emission permission to the repeater 105. In response to reception of an emission permission signal from the repeater 105, the radiation generating apparatus 106 controls the radiation source 102 to emit radiation.

The repeater 105 relays communication between the radiographic imaging apparatus 101 and the radiation generating apparatus 106. The repeater 105 is connected to the radiation generating apparatus 106 and transmits the emission-permission request signal from the radiation generating apparatus 106 to the radiographic imaging apparatus 101. The repeater 105 also transmits the emission permission signal received from the radiographic imaging apparatus 101 to the radiation generating apparatus 106. In this case, the repeater 105 can transmit and receive commands that are converted from the emission-permission request signal and the emission permission signal according to the communication method to and from the radiographic imaging apparatus 101.

Figure 2:
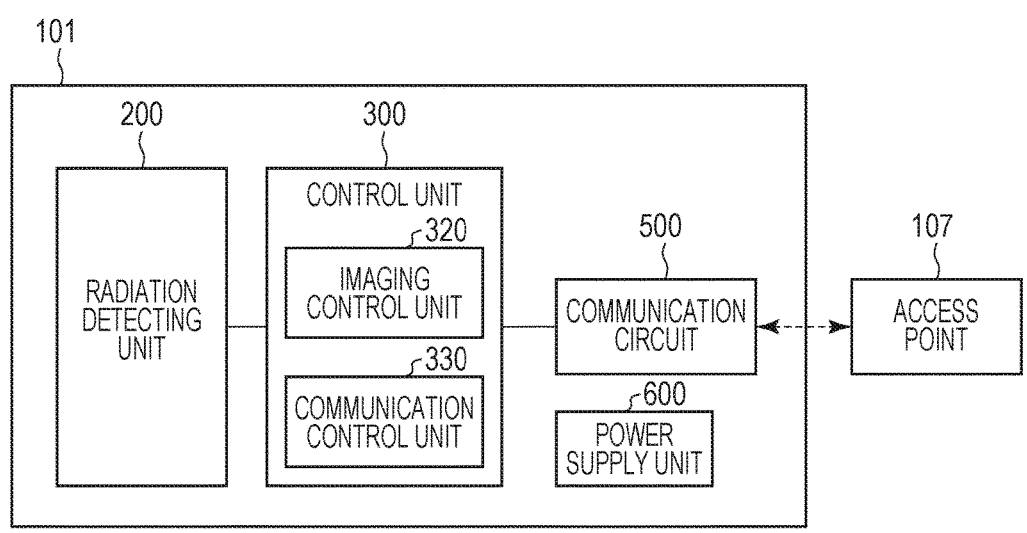
FIG. 2 is a diagram illustrating a radiographic imaging apparatus according to the first embodiment.

Referring next to FIG. 2, the radiographic imaging apparatus 101 will be described. FIG. 2 is a diagram illustrating the radiographic imaging apparatus 101. The radiographic imaging apparatus 101 includes a radiation detecting unit 200, a control unit 300, a communication circuit 500, and a power supply unit 600.

The radiation detecting unit 200 includes the function of detecting radiation emitted from the radiation source 102 and acquiring a radiation image based on the detected radiation. The control unit 300 performs overall control of the entire system of the radiographic imaging apparatus 101. The control unit 300 includes an imaging control unit 320 and a communication control unit 330. The imaging control unit 320 controls driving of the radiation detecting unit 200. The communication control unit 330 controls the operation of the communication circuit 500.

The communication circuit 500 is a circuit for wirelessly communicating with the external devices (the repeater 105 and the control apparatus 108) in a plurality of communication modes. The plurality of communication modes include at least a first communication mode and a second communication mode in which power consumption is lower than that in the first communication mode. The first communication mode is a communication mode in which transmission and reception of data with the external devices is always possible. The second communication mode is a communication mode in which a first state in which transmission and reception of data with the external devices is possible and a second state in which transmission and reception of data with the external devices is impossible are alternately repeated according to a predetermined condition.

Power consumption of the communication circuit 500 in the second state is smaller than power consumption in the first state because transmission and reception of data is impossible in the second state. For that reason, the power consumption of the communication circuit 500 is smaller in the second communication mode than in the first communication mode.

The communication control unit 330 controls the communication circuit 500 to communicate in a predetermined communication mode based on a predetermined condition. The communication control unit 330 controls the communication circuit 500 to keep, as the first communication mode, the first state in which transmission and reception of data with the external devices is possible. The communication control unit 330 controls the communication circuit 500 to alternately repeat, as the second communication mode, the first state in which transmission and reception of data with the external devices is possible and the second state in which transmission and reception of data with the external devices is impossible.

In the present embodiment, the communication control unit 330 controls the communication circuit 500 to switch the operation according to a delivery traffic indication message (DTIM) interval. In other words, the communication control unit 330 switches the communication circuit 500 from the second state to the first state in accordance with a timing when a beacon having a DTIM is transmitted from the access point 107.

The radiographic imaging apparatus 101 performs an imaging operation according to one of set imaging modes. The radiographic imaging apparatus 101 performs an imaging operation in a first imaging mode and a second imaging mode. The first imaging mode is an imaging mode in which the imaging operation is switched between the first communication mode and the second communication mode based on a predetermined condition, and the second imaging mode is an imaging mode in which an imaging operation is performed only in the second communication mode.

An example of the first imaging mode is an imaging mode in which imaging is performed with a timing of start of radiation emission matching between the radiographic imaging apparatus 101 and the repeater 105. An example of the second imaging mode is an imaging mode in which the radiographic imaging apparatus 101 detects start of emission of radiation based on the radiation detected by the radiographic imaging apparatus 101 itself.

In imaging in the first imaging mode, the communication control unit 330 controls the communication circuit 500 to change the communication mode according to an instruction to start preparation for imaging from the control apparatus 108. In imaging in the second imaging mode, the communication control unit 330 may not perform the control to change the communication mode of the communication circuit 500 according to an instruction to start preparation for imaging from the control apparatus 108. In the present embodiment, it is assumed that the radiographic imaging apparatus 101 is set in the first imaging mode. An operation in the second imaging mode will be described in detail in a second embodiment.

The power supply unit 600 includes a secondary battery and a circuit that converts electric power accumulated in the secondary battery and supplies the electric power to the components of the radiographic imaging apparatus 101.

Figure 3:
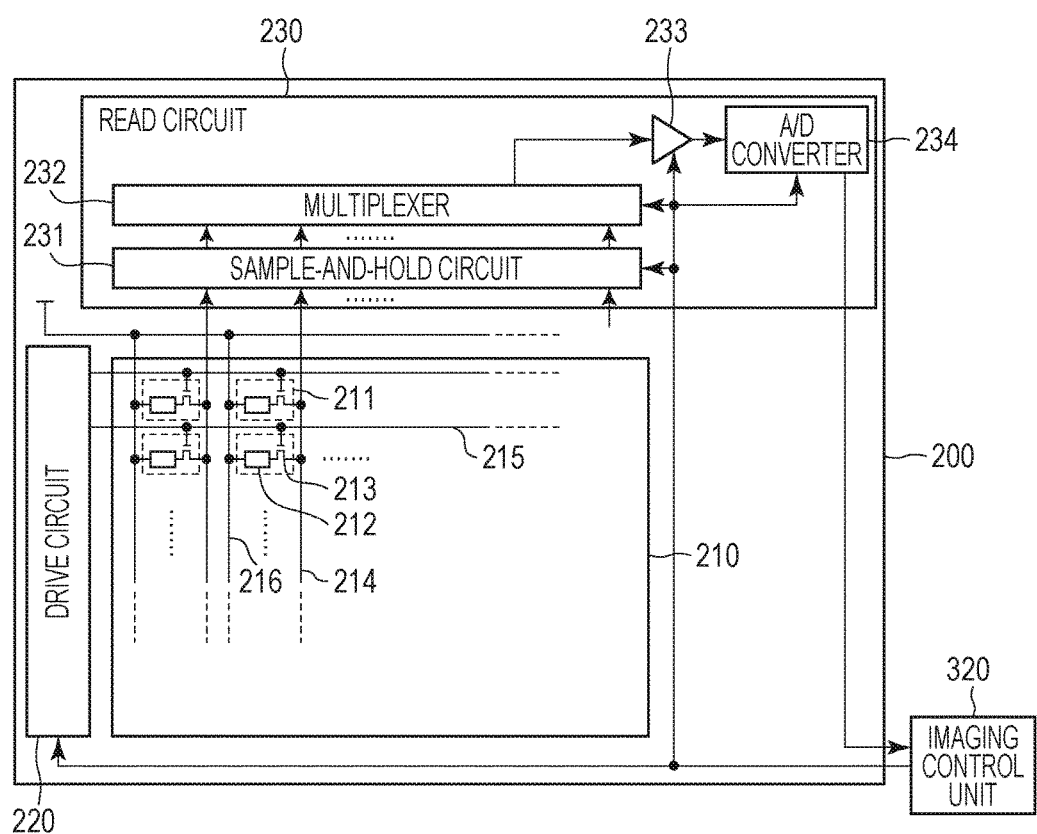
FIG. 3 is a diagram illustrating a radiation detecting unit according to the first embodiment.

Referring next to FIG. 3, the radiation detecting unit 200 will be described. The radiation detecting unit 200 includes a sensor unit 210, a drive circuit 220, and a read circuit 230. The sensor unit 210 includes a plurality of pixels 211 arranged in a two-dimensional array to form a plurality of rows and a plurality of columns. Each of the plurality of pixels 211 includes a conversion element 212 and a switching element 213.

The conversion element 212 converts incident radiation to an electric charge and accumulates the electric charge. The conversion element 212 can include a scintillator that converts radiation to visible light and a photoelectric conversion element that converts visible light to an electric charge. The conversion element 212 can directly convert radiation to an electric charge. The switching element 213 transfers the electric charges accumulated in the conversion element 212 to a signal line 214. An example of the switching element 213 is a transistor, such as a thin film transistor (TFT). The switching element 213 includes a control terminal. The switching element 213 is turned on, that is, enters a conductive state, when an ON voltage is supplied to the control terminal, and is turned off, that is, enters a nonconductive state, when an OFF voltage is supplied to the control terminal.

One terminal of the conversion element 212 is supplied with a bias voltage from the power supply unit 600 through a bias line 216. The other terminal of the conversion element 212 is connected to the signal line 214 via the switching element 213. The control terminal of the switching element 213 is connected to a drive line 215. In the sensor unit 210, a plurality of drive lines 215 extending in the row direction (in the lateral direction in FIG. 3) are arranged in the column direction (in the vertical direction in FIG. 3). The control terminals of the switching elements 213 of the pixels 211 on the same row are connected in common to each drive line 215. In the sensor unit 210, the plurality of signal lines 214 extending in the column direction are arranged in the row direction. One main terminals of the switching elements 213 of pixels 211 on the same column are connected in common to each signal line 214.

The drive circuit 220 drives the sensor units 210 according to a control signal supplied from the imaging control unit 320. Specifically, the drive circuit 220 supplies a drive signal to the control terminal of each switching element 213 through each drive line 215. The drive circuit 220 turns on the switching element 213 by setting the drive signal to ON voltage and turns off the switching element 213 by setting the drive signal to OFF voltage. When the switching element 213 is turned on, the electric charge accumulated in the conversion element 212 is transferred to the signal line 214.

The read circuit 230 reads the electric charge from the sensor unit 210 according to a control signal supplied from the imaging control unit 320, generates a signal according to the electric charge, and supplies the signal to the imaging control unit 320. The read circuit 230 includes a sample-and-hold circuit 231, a multiplexer 232, an amplifier 233, and an analog-to-digital converter 234. The sample-and-hold circuit 231 holds the electric charge read from the conversion elements 212 for each pixel row. The multiplexer 232 extracts the electric charge of pixels of one row held in the sample-and-hold circuit 231 and supplies the electric charge to the amplifier 233. The amplifier 233 amplifies the supplied electric charge and supplies the electric charge to the analog-to-digital converter 234. The analog-to-digital converter 234 converts the supplied analog signal to a digital signal (corresponding to data on radiation image described above) and supplies the digital signal to the imaging control unit 320.

Figure 4:
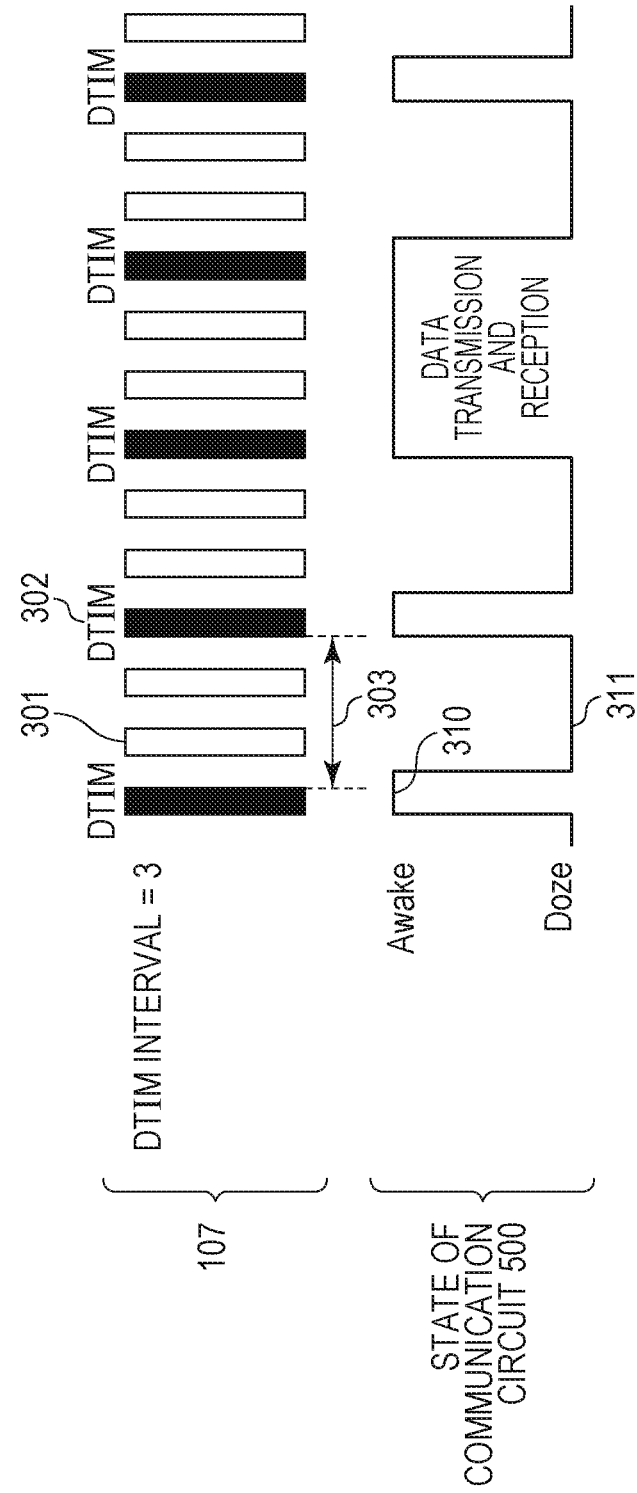
FIG. 4 is a diagram illustrating the operation of an access point and a communication circuit according to the first embodiment.

Referring next to FIG. 4, the relationship between the operation of the access point 107 and the operation of the communication circuit 500 in the second communication mode will be described. Here, a power saving operation in a wireless LAN will be described as an example of operation, but this is given for mere illustration.

The access point 107 regularly broadcasts a signal, referred to as "beacon 301", at predetermined intervals. The packet of the beacons 301 includes a delivery traffic indication message (DTIM) 310 at regular time intervals. The DTIM 310 is information for notifying presence of communication data. A value indicating the interval of the DTIM 310 embedded in the plurality of beacons 301 transmitted at predetermined intervals is referred to as "DTIM interval 303".

In FIG. 4, the DTIM time interval 303 is the transmission interval between DTIMs. The communication circuit 500 can operate in Awake state 310 (the first state) in which communication is possible and Doze state 311 (the second state) in which power supply is limited, so that communication is impossible. The communication circuit 500 shifts from the Doze state to the Awake state at the timing when DTIM information is transmitted from the access point 107 to receive the DTIM information. The communication circuit 500 shifts again to the Doze state if the beacon has no communication data, and maintains the Awake state when the beacon has communication data. Using FIG. 4 as an example, the communication mode switching operation of the communication circuit 500 will be described. For example, the interval of beacons broadcasted from the access point 107 is 100 msec and the DTIM interval is 3. In this case, the DTIM time interval is 300 msec. Therefore, the communication circuit 500 is controlled to shift from the Doze state to the Awake state every 300 msec.

Figure 5:
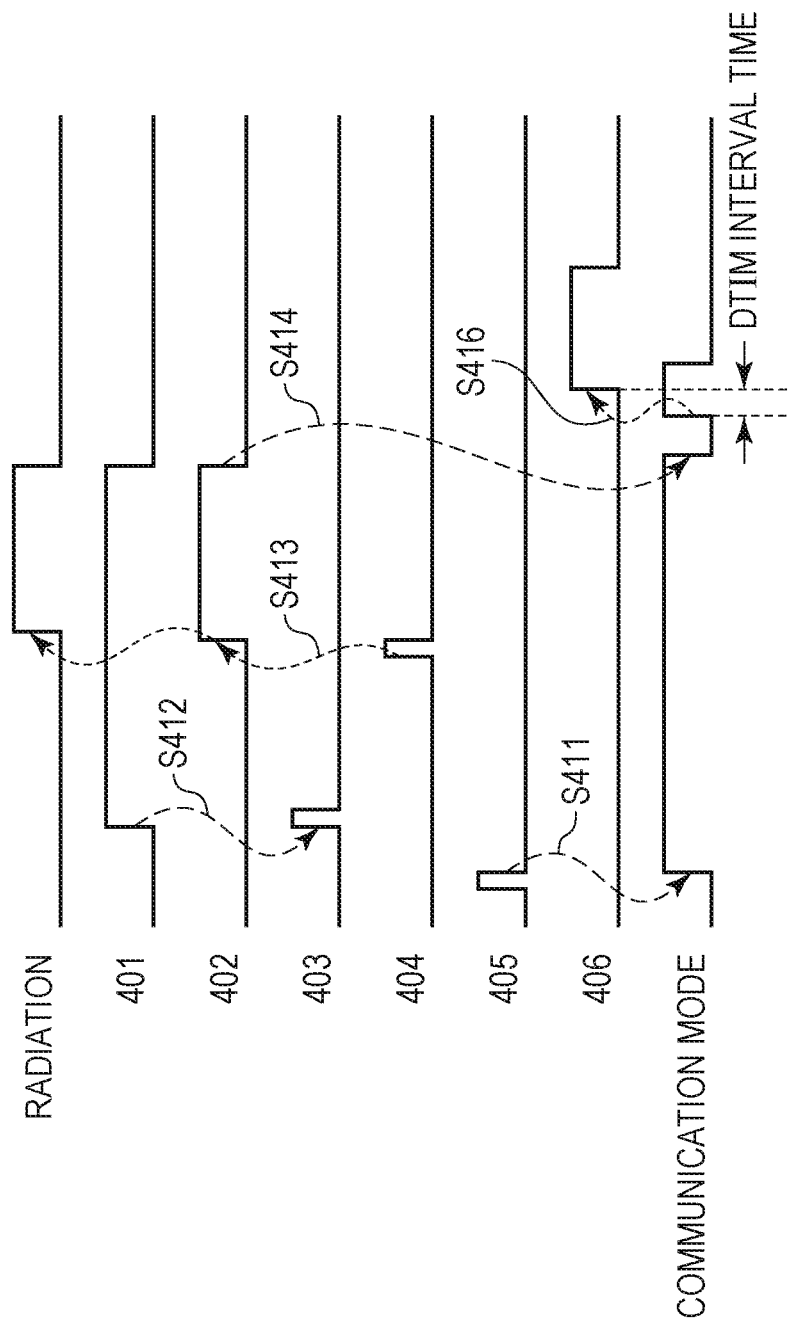
FIG. 5 is a diagram illustrating the operation of the radiographic imaging system according to the first embodiment.

Referring next to FIG. 5, the operation of the radiographic imaging system 10 will be described. First, the power to the radiographic imaging apparatus 101 is turned on by the user. In this case, the communication control unit 330 in the radiographic imaging apparatus 101 controls the communication mode of the communication circuit 500 to the second communication mode.

Next at S411, the control apparatus 108 performs control to shift the radiographic imaging apparatus 101 to an imaging possible state. First, the control apparatus 108 transmits a signal 405 to shift to the imaging possible state to the radiographic imaging apparatus 101 via the access point 107. The radiographic imaging apparatus 101 controls the communication circuit 500 so that, upon receiving the imaging possible state shift signal 405 and shifting to the imaging possible state, the communication circuit 500 operates in the first communication mode (Awake state).

Next, when at S412 the first switch 104 is pressed, the radiation generating apparatus 106 starts a preparatory operation. When the second switch 103 is pressed, the radiation generating apparatus 106 transmits a request signal 401 for emission permission to the repeater 105. The repeater 105 transmits a request signal 403 for emission permission to the radiographic imaging apparatus 101 via the access point 107.

Next, when at S413 the radiographic imaging apparatus 101 receives the emission permission request signal 403, the imaging control unit 320 controls the radiation detecting unit 200 to perform an initialization operation. After completion of the initialization operation, the imaging control unit 320 controls the radiation detecting unit 200 to perform an accumulation operation and transmits an emission permission signal 404 to the repeater 105. The repeater 105 transmits an emission permission signal 402 to the radiation generating apparatus 106. In response to receipt of the emission permission signal 402, the radiation generating apparatus 106 controls the radiation source 102 to emit radiation.

Next at S414, the radiographic imaging apparatus 101 controls the radiation detecting unit 200 to continue the accumulation operation for a predetermined accumulation period and execute a reading operation under the control of the imaging control unit 320. When the emission permission signal 402 transmitted from the repeater 105 stops, the radiographic imaging apparatus 101 shifts the communication mode to the second communication mode.

At S416, the radiographic imaging apparatus 101 switches the communication mode to the first communication mode (Awake state) the DTIM time interval before the timing when image transmission is to be performed. When transmission of a radiation image is started, the radiographic imaging apparatus 101 switches the communication mode to the first communication mode. In other words, the communication circuit 500 starts transmission of a radiation image to the control apparatus 108 after a predetermined period (DTIM time interval) has passed after the communication mode is shifted to the first communication mode. Such control prevents a delay in communicating a radiation image while saving power consumption of the communication circuit 500.

In the above control, when receiving a signal 405 to shift to the imaging possible state from the control apparatus 108, the radiographic imaging apparatus 101 controls the communication circuit 500 to operate in the first communication mode during at least a period until the request signal 403 for radiation emission permission is received from the repeater 105. This enables the radiographic imaging apparatus 101 to receive the request signal 403 for radiation emission permission without delay.

The radiographic imaging apparatus 101 controls the communication circuit 500 to operate in the first communication mode during a period until the emission permission signal 404 is transmitted to the repeater 105. This enables the radiographic imaging apparatus 101 to transmit the emission permission signal 404 without delay after receiving the permission request signal 403 for radiation emission.

The radiographic imaging apparatus 101 controls the communication circuit 500 to operate in the first communication mode during a period until transmission of a radiation image to the control apparatus 108 is started. This enables the radiographic imaging apparatus 101 to transmit the radiation image without delay.

While this is an example in which the communication mode is shifted to the second communication mode after radiation emission is stopped, the communication mode can be shifted to the second communication mode after radiation emission is started. Alternatively, the communication control unit 330 can control the communication circuit 500 to keep the first communication mode (Awake state) until image transmission is started rather than changing the communication mode to the second communication mode after radiation emission is stopped.

As described above, the radiographic imaging system of the present embodiment prevents delay in radiation emission while saving the power consumption of the wireless communication function of the radiographic imaging apparatus.

Second Embodiment

Figure 6:
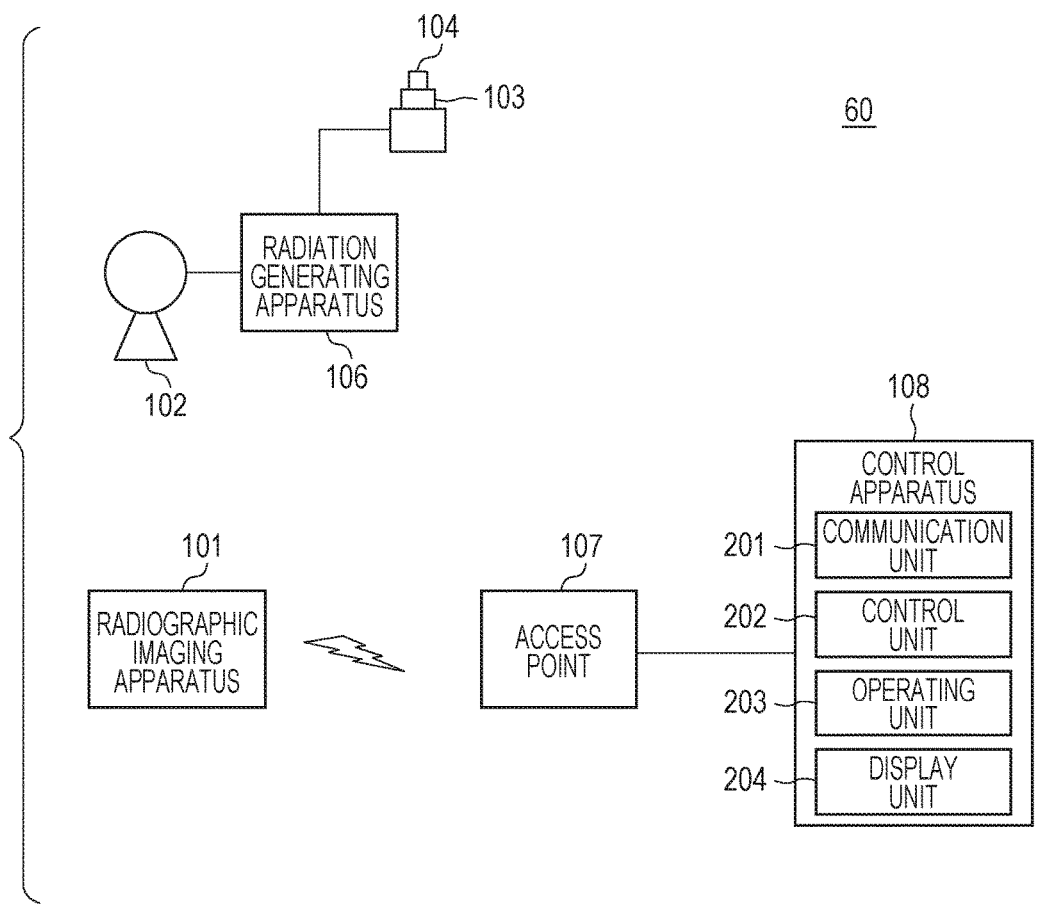
FIG. 6 is a diagram illustrating a radiographic imaging system according to a second embodiment of the present disclosure.

Referring to FIG. 6, a radiographic imaging system 60 according to a second embodiment will be described. The second embodiment differs from the first embodiment in that the radiographic imaging apparatus detects start of radiation emission and performs imaging without communicating with the radiation generating apparatus.

As illustrated in FIG. 6, the radiographic imaging system 60 includes a radiographic imaging apparatus 101, a radiation generating apparatus 106, a second switch 103 and a first switch 104 connected to the radiation generating apparatus 106, a control apparatus 108, and an access point 107. In other words, the second embodiment differs from the first embodiment in that the radiographic imaging system 60 can perform imaging without using the repeater 105. In other words, the radiographic imaging apparatus 101 detects that emission of radiation is started.

The radiographic imaging apparatus 101 includes an emission detecting function of detecting that emission of radiation is started. In this case, the control unit 300 can include the emission detecting function, or the radiation detecting unit 200 can include the emission detecting function. The radiographic imaging apparatus 101 acquires the value of an electric current flowing through the bias lines 216 of the radiation detecting unit 200, and when the acquired current value is greater than a threshold, it can be determined that emission of radiation is started. Alternatively, the radiographic imaging apparatus 101 acquires the value of an electric current flowing through the signal lines 214 of the radiation detecting unit 200, and when the current value is greater than a threshold, it can be determined that emission of radiation is started. In response to determination that emission of radiation is started, the radiographic imaging apparatus 101 can make the sensor unit 210 start an electric charge accumulation operation for imaging.

Figure 7:
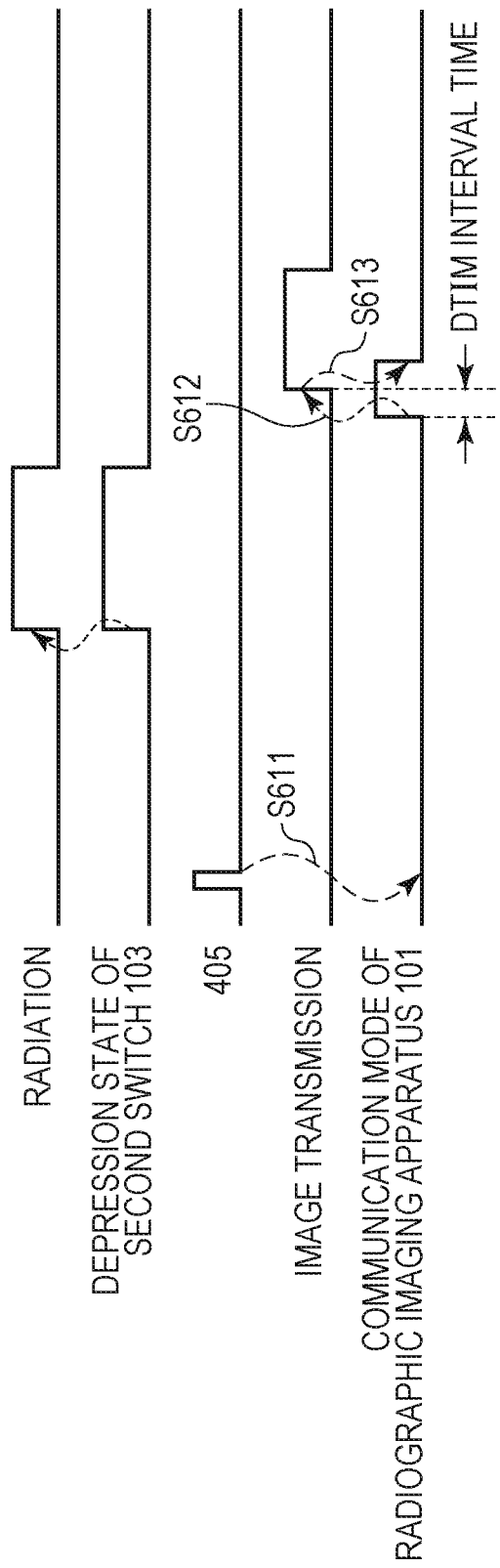
FIG. 7 is a diagram illustrating the operation of the radiographic imaging system according to the second embodiment.

Referring next to FIG. 7, the operation of the radiographic imaging system 60 of the present embodiment will be described. First at S611, the control apparatus 108 performs control to shift the radiographic imaging apparatus 101 to the imaging possible state. The control apparatus 108 first transmits a signal 405 to shift to the imaging possible state to the radiographic imaging apparatus 101 via the access point 107. The radiographic imaging apparatus 101 controls the communication circuit 500 so that, upon receiving the imaging possible state shift signal 405 and shifting to the imaging possible state, the communication circuit 500 operates in the second communication mode (Doze state). In other words, since communication with the radiation generating apparatus 106 according to depression of the second switch 103 is not generated in the present embodiment, the radiographic imaging apparatus 101 controls the communication circuit 500 to keep the second communication mode.

Next, when the second switch 103 is pressed, radiation is emitted from the radiation source 102. Upon detection of start of radiation emission, the radiographic imaging apparatus 101 starts accumulation of an electric charge. The imaging control unit 320 controls the radiation detecting unit 200 to perform the accumulation operation for a predetermined time, then read electrical signals, and generate a radiation image.

At S612, the communication control unit 330 shifts the communication mode to the first communication mode (Awake state) the DTIM interval time before the time to transmit an image. In response to start of transmission of the radiation image, the communication control unit 330 shifts the communication mode to the Doze state.

If battery duration is given higher priority than concern about delay in image transmission, the radiographic imaging apparatus 101 may not change the communication mode to the Awake state before image transmission. For example, in the case where the radiographic imaging apparatus 101 is used in a doctor's round car, so that an operation that gives priority to remaining battery life is to be performed, the operation may be performed in the second communication mode rather than switching the communication mode before image transmission.

Thus, the radiographic imaging system 60 of the present embodiment enables power saving of the wireless communication function of the radiographic imaging apparatus having the radiation detecting function.

Third Embodiment

Figure 8:
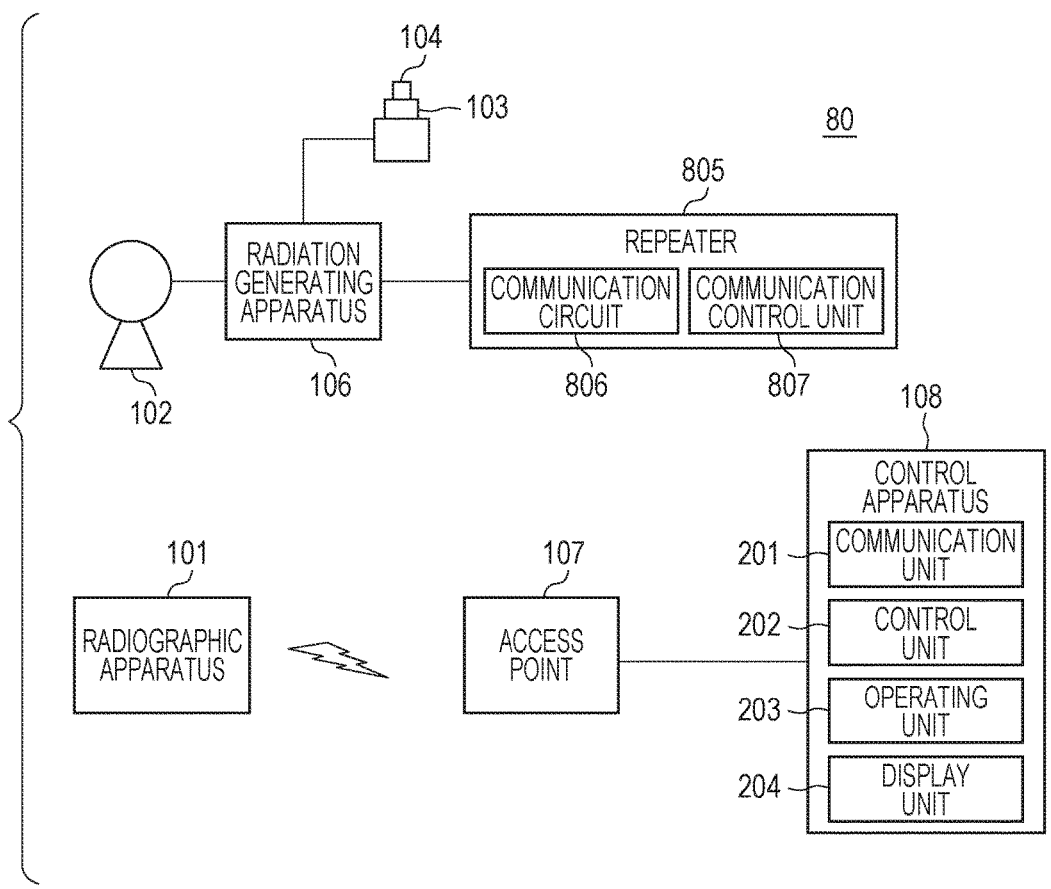
FIG. 8 is a diagram illustrating a radiographic imaging system according to a third embodiment of the present disclosure.

Referring to FIG. 8, a radiographic imaging system 80 according to a third embodiment will be described. The third embodiment differs from the first embodiment in that the repeater includes the wireless communication function and that the repeater can also switch the communication mode.

As illustrated in FIG. 8, the radiographic imaging system 80 includes a radiographic imaging apparatus 101, a radiation generating apparatus 106, a second switch 103, a first switch 104, a repeater 805, a control apparatus 108, and an access point 107.

The repeater 805 includes the wireless communication function similar to the radiographic imaging apparatus 101. The repeater 805 includes a communication circuit 806 and a communication control unit 807.

The communication circuit 806 is a circuit that wirelessly communicates with external devices (the radiographic imaging apparatus 101 and the control apparatus 108) in a plurality of communication modes. The plurality of communication modes include at least a first communication mode and a second communication mode in which power consumption is lower than that in the first communication mode. The first communication mode is a mode in which transmission and reception of data with the external devices is always possible. The second communication mode is a communication mode in which a first state (Awake state) in which transmission and reception of data with the external devices is possible and a second state (Doze state) in which transmission and reception of data with the external devices is impossible are alternately repeated according to a predetermined condition.

The communication control unit 807 controls the communication circuit 806 to communicate in a predetermined communication mode based on a predetermined condition. The communication control unit 807 controls the communication circuit 806 to keep, as the first communication mode, the first state in which transmission and reception of data with the external devices is possible. The communication control unit 807 controls the communication circuit 806 to alternately repeat, as the second communication mode, the first state in which transmission and reception of data with the external devices is possible and the second state in which transmission and reception of data with the external devices is impossible.

The communication control unit 807 controls the communication circuit 806 to switch the operation according to the DTIM interval. In other words, the communication control unit 807 switches the communication circuit 806 from the second state to the first state in accordance with the timing when a beacon having a DTIM is transmitted from the access point 107.

The repeater 805 is connected to the radiation generating apparatus 106 and transmits a request signal for emission permission from the radiation generating apparatus 106 to the radiographic imaging apparatus 101. The request signal for emission permission is transmitted to the radiographic imaging apparatus 101 via the access point 107. The repeater 805 passes an emission permission signal received from the radiographic imaging apparatus 101 to the radiation generating apparatus 106. In response to receipt of the emission permission signal, the radiation generating apparatus 106 controls the radiation source 102.

Figure 9:
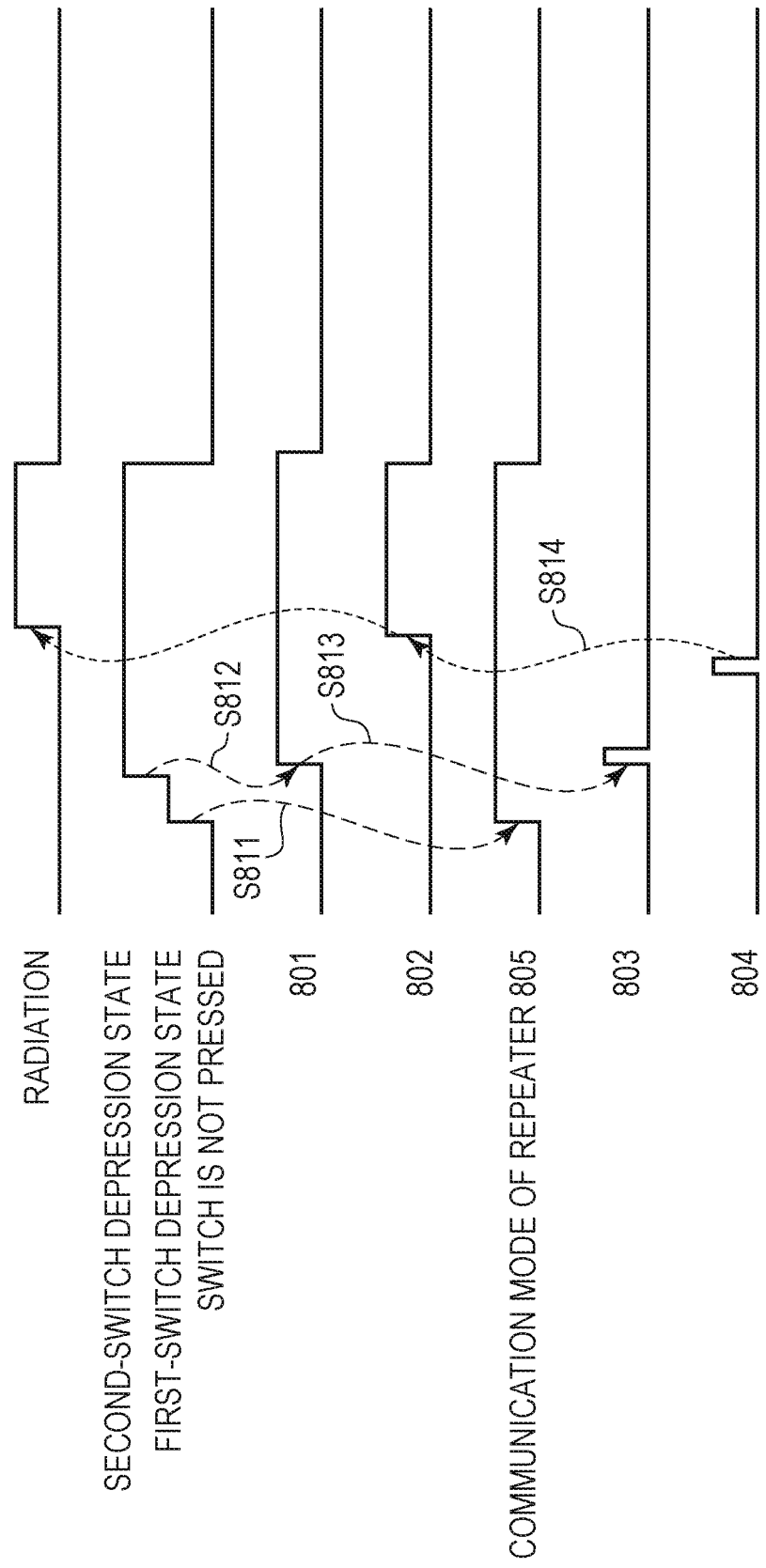
FIG. 9 is a diagram illustrating the operation of the radiographic imaging system according to the third embodiment.

Referring to FIG. 9, the operation of the radiographic imaging system 80 of the present embodiment will be described. First at S811, in response to depression of the first switch 104, the repeater 805 controls the communication mode to the first communication mode (Awake state).

Next at S812, an emission request signal 801 is transmitted to the repeater 805 in response to depression of the second switch 103. At S813, the repeater 805 wirelessly transmits an emission request signal 803 to the radiographic imaging apparatus 101.

At S814, after completion of preparation for imaging (an initialization operation of the radiation detecting unit 200), the radiographic imaging apparatus 101 transmits an emission permission signal 804 to the repeater 805. Upon receipt of the emission permission signal 804, the repeater 805 transmits an emission permission signal 802 to the radiation generating apparatus 106. The radiation generating apparatus 106 controls the radiation source 102 to emit radiation.

When emission of radiation ends, the repeater 805 switches the communication mode to the second communication mode (Doze state).

The repeater 805 can switch its communication mode by receiving a predetermined signal transmitted from the control apparatus 108 or a predetermined signal transmitted from the radiographic imaging apparatus 101. For example, the control apparatus 108 can transmit the predetermined signal to the repeater 805 according to the timing of transmitting a signal to shift to an imaging possible state to the radiographic imaging apparatus 101. For example, the radiographic imaging apparatus 101 can transmit the predetermined signal to the repeater 805 in response to entering an imaging possible state.

Thus, the configuration of the radiographic imaging system 80 of the present embodiment in which the repeater 805 includes a wireless communication function saves the power consumption of the wireless communication function of the radiographic imaging system 80.

Fourth Embodiment

Figure 10:
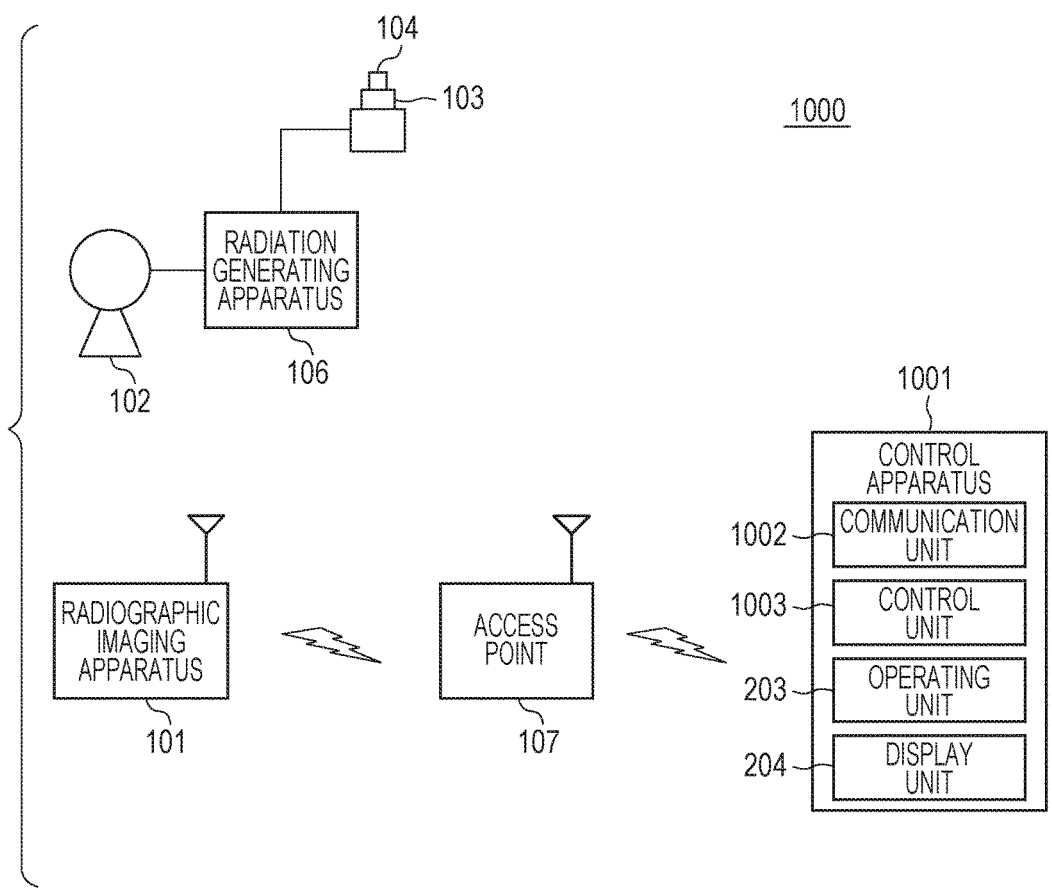
FIG. 10 is a diagram illustrating a radiographic imaging system according to a fourth embodiment of the present disclosure.

Referring to FIG. 10, a radiographic imaging system 1000 according to a fourth embodiment will be described. The fourth embodiment differs from the second embodiment in that the control apparatus can also switch the communication mode.

As illustrated in FIG. 10, the radiographic imaging system 1000 includes a radiographic imaging apparatus 101, a radiation generating apparatus 106, a second switch 103, a first switch 104, a control apparatus 1001, and an access point 107.

The control apparatus 1001 includes a wireless communication function, and its communication mode includes a first communication mode and a second communication mode. The radiographic imaging apparatus 101 includes an emission detecting function of detecting that emission of radiation is started. The emission detecting function is the same as that of the second embodiment. In response to determination that emission of radiation is started, the radiographic imaging apparatus 101 can make the sensor unit 210 start an electric charge accumulation operation for imaging.

Figure 11:
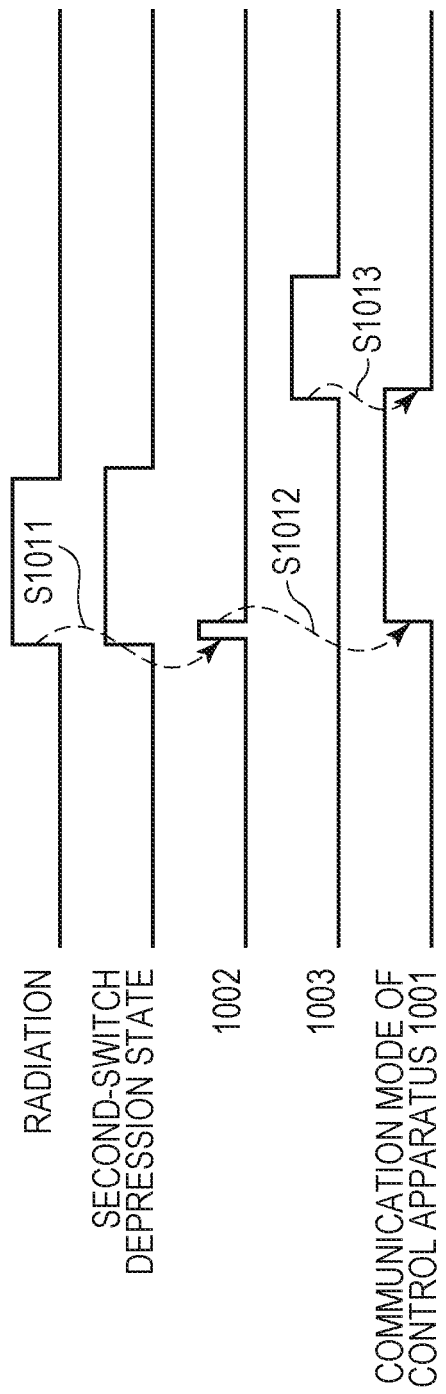
FIG. 11 is a diagram illustrating the operation of the radiographic imaging system according to the fourth embodiment.

Referring to FIG. 11, the operation of the radiographic imaging system 1000 of the present embodiment will be described. At S1011, upon detection of emission of radiation, the radiographic imaging apparatus 101 transmits an imaging start signal 1002 to the control apparatus 1001. Upon reception of the imaging start signal 1002 at S1012, the control apparatus 1001 switches the communication mode to the first communication mode (Awake state). At S1013, the control apparatus 1001 starts to receive a radiation image 1003 transmitted from the radiographic imaging apparatus 101, and thereafter switches the communication mode to the second communication mode (Doze state). Since the control apparatus 1001 switches the communication mode to the Awake state before reception of a radiation image, the radiation image can be received without delay while saving power consumption. Using the imaging start signal from the radiographic imaging apparatus 101 as a trigger eliminates the need for special wiring for communication and additional signals.

The method for switching the communication mode according to reception of the imaging start signal in the present embodiment is given for mere illustration. Like the control apparatus 1001, the radiographic imaging apparatus 101 can shift the communication mode to the first communication mode when shifting to the imaging possible state.

Thus, the configuration of the radiographic imaging system 1000 of the present embodiment in which the control apparatus 1001 includes a wireless communication function saves the power consumption of the wireless communication function of the radiographic imaging system 1000.

Fifth Embodiment

Figure 12:
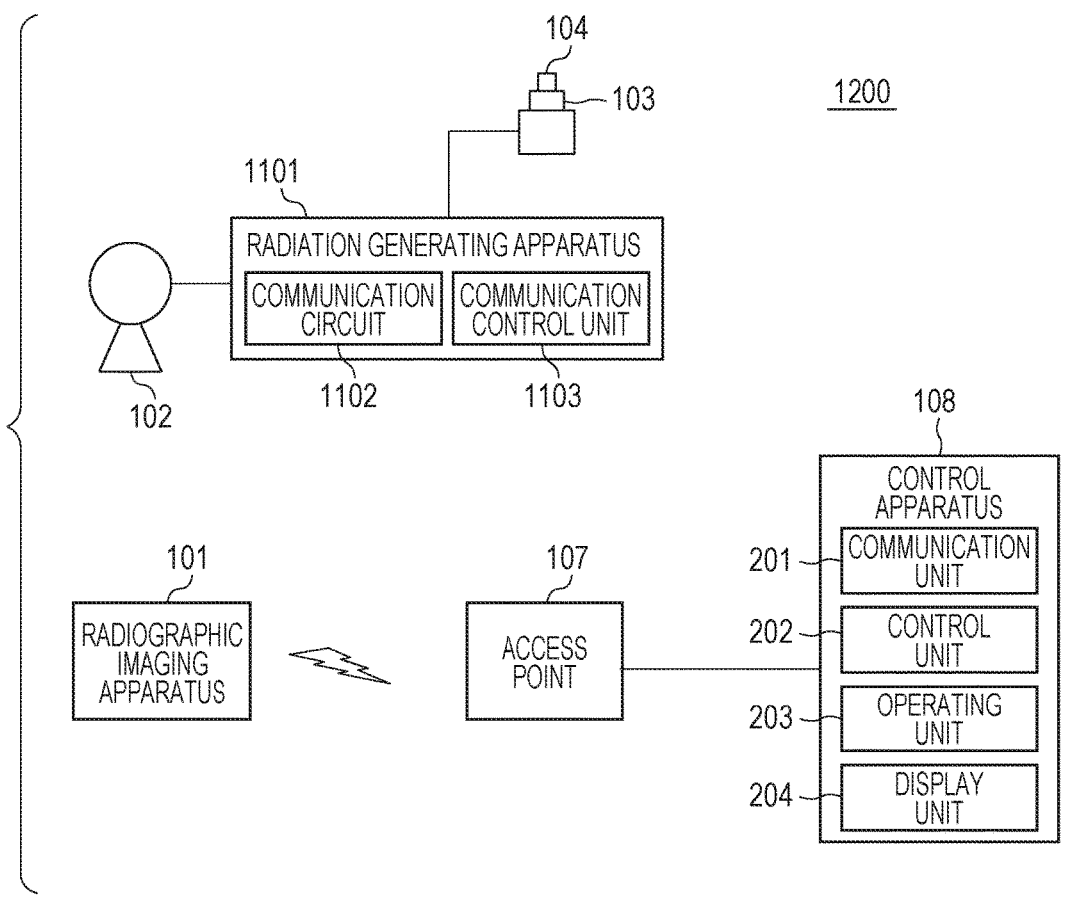
FIG. 12 is a diagram illustrating a radiographic imaging system according to a fifth embodiment of the present disclosure.

Referring to FIG. 12, a radiographic imaging system 1200 according to a fifth embodiment will be described. The fifth embodiment differs from the other embodiments in that the radiation generating apparatus can also switch the communication mode.

As illustrated in FIG. 12, the radiographic imaging system 1200 includes a radiographic imaging apparatus 101, a radiation generating apparatus 1101, a second switch 103, a first switch 104, a control apparatus 108, and an access point 107.

Like the radiographic imaging apparatus 101, the radiation generating apparatus 1101 includes a wireless communication function. The radiation generating apparatus 1101 includes a communication circuit 1102 and a communication control unit 1103.

The communication circuit 1102 is a circuit that wirelessly communicates with the external devices (the radiographic imaging apparatus 101 and the control apparatus 108) in a plurality of communication modes. The plurality of communication modes includes at least a first communication mode and a second communication mode in which power consumption is lower than that in the first communication mode. The first communication mode is a communication mode in which transmission and reception of data with the external devices is always possible. The second communication mode is a communication mode in which a first state (Awake) in which transmission and reception of data with the external devices is possible and a second state (Doze) in which transmission and reception of data with the external devices is impossible are alternately repeated according to a predetermined condition.

The communication control unit 1103 controls the communication circuit 1102 to communicate in a predetermined communication mode based on a predetermined condition. The communication control unit 1103 controls the communication circuit 1102 to keep, as the first communication mode, the first state in which transmission and reception of data with the external devices is possible. The communication control unit 1103 controls the communication circuit 1102 to alternately repeat, as the second communication mode, the first state in which transmission and reception of data with the external devices is possible and the second state in which transmission and reception of data with the external devices is impossible. The communication control unit 1103 controls the communication circuit 1102 to switch the operation according to a DTIM interval. In other words, the communication control unit 1103 switches the communication circuit 1102 from the second state to the first state in accordance with the timing when a beacon having a DTIM is transmitted from the access point 107.

Referring to FIG. 13, the operation of the radiographic imaging system 1200 of the present embodiment will be described. When at S1211 the first switch 104 is pressed, the radiation generating apparatus 1101 shifts the communication mode of the communication circuit 1102 to the first communication mode (Awake). When at S1212, the second switch 103 is pressed and the radiation generating apparatus 1101 transmits a request signal 1201 for emission permission to the radiographic imaging apparatus 101.

At S1213, the radiographic imaging apparatus 101 transmits an emission permission signal 1202 to the radiation generating apparatus 1101. Upon receipt of the emission permission signal 1202, the radiation generating apparatus 1101 controls the radiation source 102 to emit radiation. Thereafter, the communication mode of the radiation generating apparatus 1101 is shifted to the Doze state.

Thus, the configuration of the radiographic imaging system 1200 of the present embodiment in which the radiation generating apparatus 1101 includes a wireless communication function saves the power consumption of the wireless communication function of the radiographic imaging system 1200.

OTHER EMBODIMENTS

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-180327 filed Sep. 15, 2016, which is hereby incorporated by reference herein in its entirety.

What is claimed is:

1. A radiographic imaging system comprising:
a repeater configured to control timing to emit radiation from a radiation source;
a radiographic imaging apparatus comprising a communication circuit configured to perform wireless communication in a first communication mode and a second communication mode in which power consumption is lower than that in the first communication mode; and
a control apparatus configured to control the radiographic imaging apparatus,
wherein the radiographic imaging apparatus further comprises a communication control unit configured to control the communication circuit such that, when receiving a signal to shift to an imaging possible state, the communication circuit operates in the first communication mode until receiving a signal for permitting emission of radiation from the repeater.

2. The radiographic imaging system according to claim 1, wherein the communication control unit controls the communication circuit to alternately repeat a first state in which transmission and reception of data is possible and a second state in which transmission and reception of data is impossible as the second communication mode.

3. The radiographic imaging system according to claim 1, wherein the communication control unit controls the communication circuit to operate in the first communication mode during a period from receipt of the signal to shift to an imaging possible state until transmission of a permission signal for emission of radiation to the repeater.

4. The radiographic imaging system according to claim 1, wherein the communication control unit controls the communication circuit to operate in the first communication mode during a period from receipt of the signal to shift to an imaging possible state until receipt of a signal indicating completion of radiation emission from the repeater.

5. The radiographic imaging system according to claim 1,
wherein the communication control unit controls the communication circuit to operate in the first communication mode during a period from receipt of the signal to shift to an imaging possible state until start of transmission of a radiation image to the control apparatus, and
wherein the communication control unit shifts the communication circuit from the first communication mode to the second communication mode after transmission of the radiation image to the control apparatus is started.

6. The radiographic imaging system according to claim 1,
wherein the communication control unit shifts the communication circuit from the second communication mode to the first communication mode, and
wherein, after a predetermined period has passed after shifting to the first communication mode, the communication circuit starts transmission of the radiation image to the control apparatus.

7. The radiographic imaging system according to claim 1,
wherein the radiographic imaging apparatus performs an imaging operation in a first imaging mode and a second imaging mode,
wherein, in the first imaging mode, the radiographic imaging apparatus performs the imaging operation while switching between the first communication mode and the second communication mode based on a predetermined condition, and
wherein, in the second imaging mode, the radiographic imaging apparatus performs the imaging operation in the second communication mode.

8. The radiographic imaging system according to claim 7,
wherein the first imaging mode is an imaging mode in which imaging is performed with a timing of start of radiation emission matching between the radiographic imaging apparatus and the repeater, and
wherein the second imaging mode is an imaging mode in which the radiographic imaging apparatus detects start of radiation emission based on radiation detected by the radiographic imaging apparatus.

9. The radiographic imaging system according to claim 7, wherein, in performing imaging in the first imaging mode, the communication control unit performs control to change a communication mode of the communication circuit according to an instruction to start preparation for imaging from the control apparatus, and wherein, in performing imaging in the second imaging mode, the communication control unit does not perform the control to change the communication mode of the communication circuit based on an instruction to start preparation for imaging from the control apparatus.

10. A radiographic imaging apparatus comprising:

a communication circuit configured to wirelessly communicate with an external device in a first communication mode and a second communication mode in which power consumption is lower than that in the first communication mode; and a communication control unit configured to control the communication circuit such that, when receiving an instruction to shift to an imaging possible state, the communication circuit operates in the first communication mode until receiving a permission signal for emission of radiation from a repeater configured to control timing to emit radiation from a radiation source.

11. A method for controlling a radiographic imaging system, the method comprising the steps of:

wirelessly communicating with an external device in a first communication mode and a second communication mode in which power consumption is lower than that in the first communication mode; and receiving an instruction to shift to an imaging possible state, wherein upon receipt of the instruction to shift to the imaging possible state, the radiographic imaging apparatus operates in the first communication mode until receipt of a signal for emission of radiation.

* * * * *